(12) United States Patent
Matsuoka et al.

(10) Patent No.: US 11,874,430 B2
(45) Date of Patent: Jan. 16, 2024

(54) SOLAR RADIATION HEAT SENSOR DEVICE AND SOLAR RADIATION HEAT MEASURING METHOD

(71) Applicant: Nippon Telegraph and Telephone Corporation, Tokyo (JP)

(72) Inventors: Hiroto Matsuoka, Tokyo (JP); Takako Ishihara, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 204 days.

(21) Appl. No.: 17/427,175

(22) PCT Filed: Feb. 19, 2020

(86) PCT No.: PCT/JP2020/006553
§ 371 (c)(1),
(2) Date: Jul. 30, 2021

(87) PCT Pub. No.: WO2020/179453
PCT Pub. Date: Sep. 10, 2020

(65) Prior Publication Data
US 2022/0146709 A1    May 12, 2022

(30) Foreign Application Priority Data

Mar. 4, 2019   (JP) .................. 2019-038238

(51) Int. Cl.
*G01W 1/12*   (2006.01)
(52) U.S. Cl.
CPC ................... *G01W 1/12* (2013.01)

(58) Field of Classification Search
CPC ....... G01W 1/12; G01J 5/0215; G01J 5/0265; G01J 5/041; G01J 5/10; G01J 5/802; G01J 2001/4266; G01J 2005/103; G01K 17/20; A61B 5/01
See application file for complete search history.

(56) References Cited

FOREIGN PATENT DOCUMENTS

| JP | S63173989 A | | 7/1988 |
|----|----|----|----|
| JP | 10104363 A | * | 4/1998 |
| JP | H10104363 A | | 4/1998 |
| JP | 2013228374 A | * | 11/2013 |

(Continued)

OTHER PUBLICATIONS

JP-2016109518-A_Translated (Year: 2016).*

(Continued)

*Primary Examiner* — Alessandro V Amari
*Assistant Examiner* — Michael J Singletary
(74) *Attorney, Agent, or Firm* — Slater Matsil, LLP

(57) ABSTRACT

A solar radiation heat sensor device includes: a black plate having a black surface; a silver plate having a silvery-white surface; a casing that supports the black plate and the silver plate in such a manner as to be exposed to an outside with the black surface and the silvery-white surface facing the same direction; a thermistor which is accommodated in the casing and is configured to measure temperatures of each of the black plate and the silver plate; and a processor configured to calculate a solar radiation heat amount based on a difference between the temperature of the black plate and the temperature of the silver plate, the temperatures being measured by the thermistor.

18 Claims, 11 Drawing Sheets

(56) References Cited

FOREIGN PATENT DOCUMENTS

| | | | |
|---|---|---|---|
| JP | 2013228374 A | | 11/2013 |
| JP | 2016109518 A | * | 6/2016 |
| JP | 2018116584 A | | 7/2018 |
| JP | 2018189539 A | | 11/2018 |

OTHER PUBLICATIONS

JP-2013228374-A_Translated (Year: 2013).*
JP-10104363-A_Translated (Year: 1998).*
Saito, "Heat Environment Evaluation by WBGT Index and JIS Stone of Electronic WBGT Measuring Instrument," National Institute of Occupational Safety and Health, Japan, Jan. 25, 2019 (Reading Day), https://www.jniosh.johas.go.jp/publication/mail_mag/2017/102-column-1.html, 7 pgs.

* cited by examiner

SOLAR RADIATION HEAT SENSOR DEVICE AND SOLAR RADIATION HEAT MEASURING METHOD

CROSS-REFERENCE TO RELATED APPLICATIONS

This application is a national phase entry of PCT Application No. PCT/JP2020/006553, filed on Feb. 19, 2020, which claims priority to Japanese Application No. 2019-038238, filed on Mar. 4, 2019, which applications are hereby incorporated herein by reference.

TECHNICAL FIELD

The present invention relates to a solar radiation heat sensor device and a solar radiation heat measurement method.

BACKGROUND

Exposure to direct sunlight is one cause of heatstroke, sunstroke, or other symptoms. A wet-bulb globe temperature (WBGT) index is used as one indicator for measuring and evaluating a hot environment in order to prevent heatstroke. A WBGT measuring instrument for calculating the WBGT index includes a globe temperature sensor. A conventional WBGT measuring instrument uses the globe temperature sensor to measure a radiant heat from, for example, sunlight, and calculates a heatstroke index such as the WBGT index (refer to NPL 1).

The conventional WBGT measuring instrument can obtain an index in an environment in which the measuring instrument is installed. However, the amount of solar radiation heat actually received by an individual user greatly differs depending on whether shadow is casted on a location of each user, for example. Thus, there is a demand for a solar radiation heat sensor device capable of measuring the solar radiation heat amount for each user.

It is necessary to suppress an influence of conduction of heat to the body of the conventional WBGT measuring instrument in order for the globe temperature sensor used for the WBGT measuring instrument to accurately measure radiant heat from, for example, sunlight. Thus, the globe temperature sensor and the casing of the measuring instrument are thermally separated from each other sufficiently, and the size of the globe temperature sensor itself is increased to improve heat capacity. As a result, when the conventional globe temperature sensor is used to construct a solar radiation heat sensor device, the size of the casing becomes larger and the weight of the casing also becomes larger, leading to a difficulty in attaching the solar radiation heat sensor device to, for example, clothes worn by the user.

CITATION LIST

Non Patent Literature

NPL 1—"WBGT Shisuu ni Yoru Shonetsu Kankyou Hyouka to Denshishiki WBGT Sokuteiki no JIS Ka ni Tsuite (Evaluation of hot environment by WBGT index and specification of electronic WBGT measuring instrument by JIS)", online, May, 12, 2017, National Institute of Occupational Safety and Health, Japan, searched on Feb., 19, 2019, the Internet, <https://www.jniosh.johas.go.jp/publication/mail_mag/2017/102-column-1.html>.

SUMMARY

Technical Problem

When the conventional technology is applied to reduce the size and weight of the solar radiation heat sensor device including a globe temperature sensor so that the solar radiation heat sensor device can be attached to clothes worn by the user, the globe temperature sensor and the casing cannot be thermally separated from each other sufficiently, which causes an influence due to the temperature of the casing, for example. As a result, when the solar radiation heat sensor device can be attached to clothes, it is difficult to accurately measure the solar radiation heat amount.

Embodiments of the present invention have been made in order to solve the above-mentioned problem, and has an object to provide a solar radiation heat sensor device that can be attached to clothes of a user.

Means for Solving the Problem

In order to solve the above-mentioned problem, a solar radiation heat sensor device according to embodiments of the present invention includes a first plate having a black surface; a second plate having a silvery-white surface; a casing that supports the first plate and the second plate in such a manner as to be exposed to an outside with the black surface and the silvery-white surface facing the same direction; a temperature sensor which is accommodated in the casing and is configured to measure temperatures of each of the first plate and the second plate; and a processor configured to calculate a solar radiation heat amount based on a difference between the temperature of the first plate and the temperature of the second plate, the temperatures being measured by the temperature sensor.

Furthermore, in the solar radiation heat sensor device according to embodiments of the present invention, the first plate and the second plate may be provided in the casing so as to be away from each other in plain view.

Furthermore, in the solar radiation heat sensor device according to embodiments of the present invention, the first plate and the second plate may be formed to have the same shape and size.

Furthermore, in the solar radiation heat sensor device according to embodiments of the present invention, the first plate and the second plate may be formed to have a disk shape.

Furthermore, the solar radiation heat sensor device according to embodiments of the present invention may further include heat insulating materials provided between the first plate and the casing and between the second plate and the casing.

Furthermore, the solar radiation heat sensor device according to embodiments of the present invention may further include: a control circuit including the processor and configured to control an operation of the temperature sensor; and a battery configured to supply power to the control circuit, and the control circuit and the battery are accommodated in the casing.

Furthermore, the solar radiation heat sensor device according to embodiments of the present invention may further include a communication control circuit configured to control communication with the outside.

In order to solve the above-mentioned problem, a solar radiation heat measurement method according to embodiments of the present invention is a solar radiation heat measurement method, which is executed by a solar radiation heat sensor device that includes a first plate having a black surface; a second plate having a silvery-white surface; a casing that supports the first plate and the second plate in such a manner as to be exposed to an outside with the black surface and the silvery-white surface facing the same direction; a temperature sensor which is accommodated in the casing; and a processor, the solar radiation heat measurement method including: a first step of measuring, by the temperature sensor, temperatures of each of the first plate and the second plate; and a second step of calculating, by the processor, a solar radiation heat amount based on a difference between the temperature of the first plate and the temperature of the second plate, the temperatures being measured in the first step.

Effects of Embodiments of the Invention

According to embodiments of the present invention, the solar radiation heat amount is calculated based on a difference between the temperature of the first plate having a black surface and the temperature of the second plate having a silvery-white surface, and thus it is possible to realize a solar radiation heat sensor device that can be attached to clothes of the user.

DETAILED DESCRIPTION OF ILLUSTRATIVE EMBODIMENTS

Now, description is given in detail of an embodiment of the present invention with reference to FIG. 1 to FIG. 11.

A solar radiation heat sensor device 1 according to this embodiment has such structure as to be attachable to clothes 2 worn by a user, and measures an amount of radiant (hereinafter sometimes referred to as "solar radiation") heat from, for example, sunlight.

Figure 1:
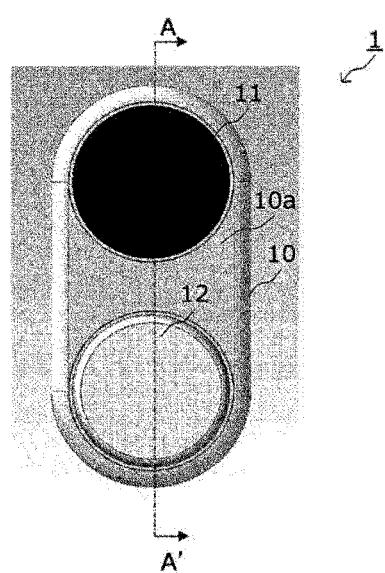
FIG. 1 is an external view of a solar radiation heat sensor device according to an embodiment of the present invention.
Figure 2:
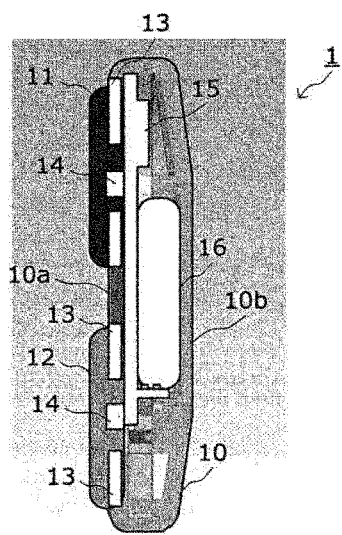
FIG. 2 is a cross-sectional diagram of FIG. 1 taken along an A-A' line.

As illustrated in FIG. 1 and FIG. 2, the solar radiation heat sensor device 1 according to this embodiment includes a casing 10, a black plate (first plate) 11 having a black surface, and a silver plate (second plate) 12 having a silvery-white surface. The black plate 11 and the silver plate 12 are exposed on a top surface 10a of the casing 10. The black plate 11 and the silver plate 12 are arranged on the casing 10 via a heat insulating material 13. A thermistor 14 is provided as a temperature sensor on each of the black plate 11 and the silver plate 12 on the inner side of the casing 10. The casing 10 accommodates a control board 15 and a battery 16.

Figure 3:
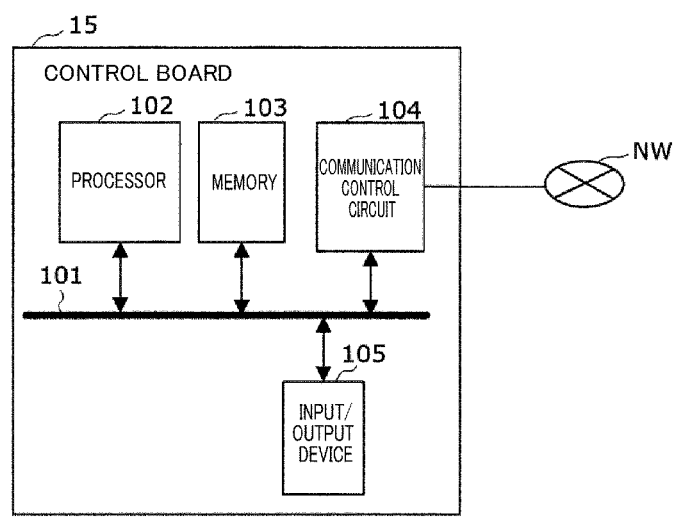
FIG. 3 is a block diagram illustrating a configuration of a control board according to this embodiment.

As illustrated in FIG. 3, the control board (control circuit) 15 can be implemented by, for example, a computer including a processor 102 such as a CPU, a memory 103, a communication control circuit 104, and an input/output device 105, which are connected to one another via a bus 101, and a program for controlling those hardware resources.

The memory 103 stores in advance a program for the processor 102 to perform various kinds of control or calculation.

The communication control circuit 104 is an interface circuit for communicating with various kinds of external electronic devices via a communication network NW.

A calculation interface and an antenna supporting wireless data communication standards such as LTE, 3G, wireless LAN, Bluetooth (registered trademark) are used as the communication control circuit 104.

The input/output device 105 is constructed by an I/O terminal for inputting a signal from an external device or outputting a signal to the external device.

In this embodiment, the casing 10 is, for example, a container formed to be substantially a cuboid having the top surface 10a and a bottom surface 10b being squares with rounded corners in plain view. The casing 10 can be formed of a polymer material such as ABS resin, rubber, or silicone resin.

The casing 10 is formed to have a size of, for example, about 5 cm×3 cm×1 cm such that the casing 10 can be attached to clothes of the user. For example, a stud (male member) of a snap button can be provided on the bottom surface 10b like "hitoe (registered trademark) transmitter 01" made by NTT DOCOMO, INC. In this case, a socket and a stud (female member) provided on the clothes 2 worn by the user can be used to construct the solar radiation heat sensor device 1 so as to be attachable to the clothes 2.

The casing 10 supports the black plate 11 and the silver plate 12 such that the black surface and the silvery-white surface are each exposed to the outside in the same direction. Two holes are formed on one top surface 10a of the casing 10, and the black plate 11 and the silver plate 12 engage with those holes. As illustrated in FIG. 2, the back surfaces of the black plate 11 and the silver plate 12 are arranged so as to be in contact with the heat insulating material 13 and the thermistor 14. The top surface 10a of the casing 10 is a surface in contact with the outside air, and the bottom surface 10b is a surface in contact with the clothes 2 and a human body 3 of the user.

The black plate 11 and the silver plate 12 can be formed of the same material such that the specific heat and heat conduction are the same. For example, the black plate 11 and the silver plate 12 can be formed by using resin or a metal material, for example. Furthermore, the black plate 11 and the silver plate 12 can be formed to have the same shape such as a plate shape and the same size such that the head capacity is the same.

Furthermore, the thicknesses of the black plate 11 and the silver plate 12 formed to have a plate shape can be set in consideration of a time response or noise due to the heat capacity.

As illustrated in FIG. 1 and FIG. 2, at least a surface of the black plate 11, which is exposed to the outside on the top surface 10a of the casing 10, is set to be black. Furthermore, at least a surface of the silver plate 12, which is exposed to the outside on the top surface 10a of the casing 10, is set to be silvery-white.

The surface of the black plate 11 can be subjected to blackening processing by, for example, iron oxide so as to absorb radiant heat (heat radiation) from, for example, sunlight as much as possible. For example, a matte blackened surface is formed. The absorption rate of radiation energy, namely, the radiation rate of radiation energy is about 0.95 for the black plate 11 subjected to such surface processing.

The surface of the silver plate 12 is subjected to surface processing by, for example, glossy chrome plating so as to reflect radiant heat from, for example, sunlight as much as possible. The absorption rate (radiation rate) of radiation energy is about 0.06 for the silver plate 12 subjected to such mirror processing.

For example, as illustrated in FIG. 1, the black plate 11 and the silver plate 12 are formed to have a disk shape, and engage with holes formed on the casing 10. One surface of the black plate 11 and one surface of the silver plate 12 are formed such that areas of those surfaces exposed to the outside on the top surface 10a of the casing 10 are equal to each other. As illustrated in FIG. 2, the other surface of the black plate 11 and the other surface of the silver plate 12 are each in contact with the heat insulating material 13 and the thermistor 14.

The black plate 11 and the silver plate 12 are desired to be arranged on the top surface 10a of the casing 10 so as to be away from each other as far as possible. The purpose is to prevent the silver plate 12 from being influenced by radiant heat from, for example, sunlight absorbed by the black plate 11 to the extent possible.

The heat insulating material 13 is arranged between the black plate 11 and the casing 10, and thermally separates the black plate 11 from the casing 10. For example, the heat insulating material 13 has a periphery similar to that of the black plate 11, and can have such a shape that a hole is formed on the center. Furthermore, the heat insulating material 13 having a shape similar to that of the heat insulating material 13 used for the black plate 11 is also used for the silver plate 12, and the heat insulating material 13 is arranged between the silver plate 12 and the casing 10 to thermally separate the silver plate 12 from the casing 10.

As illustrated in FIG. 2, the thermistor 14 is provided on the back surfaces of the black plate 11 and the silver plate 12. More specifically, the thermistor 14 is arranged at a position of the hole formed on the heat insulating material 13 provided on each back surface of the black plate 11 and the silver plate 12. The thermistor 14 is used as a temperature sensor for detecting each temperature of the black plate 11 and the silver plate 12. A resistance value detected by the thermistor 14 is converted by the processor 102 mounted on the control board 15 into a black plate temperature indicating the temperature of the black plate 11 and a silver plate temperature indicating the temperature of the silver plate 12 to be output.

The control board 15 includes the processor 102, and controls the operation of the thermistor 14. More specifically, the processor 102 calculates a difference between the black plate temperature and the silver plate temperature, reads a relationship between a solar radiation heat amount and the difference between the black plate temperature and the silver plate temperature, which is stored in the memory 103 in advance, and outputs a solar radiation heat amount corresponding to the calculated difference between the black plate temperature and the silver plate temperature.

Various kinds of batteries such as a button lithium battery and a lithium air battery can be used as the battery 16. The battery 16 supplies power to the control board 15.

Figure 4:
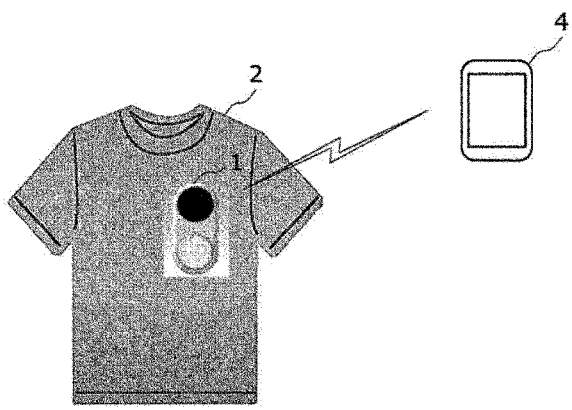
FIG. 4 is a diagram illustrating a specific example in which the solar radiation heat sensor device according to this embodiment is attached to clothes.

As illustrated in FIG. 4, the communication control circuit 104 may send out the difference between the black plate temperature and the silver plate temperature calculated by the processor 102 to an external terminal 4 via the communication network NW. Alternatively, the communication control circuit 104 may transmit the measured black plate temperature and silver plate temperature to the terminal 4 such as an external server or a smartphone. In this case, the difference between the black plate temperature and the silver plate temperature is calculated by the terminal 4 such as an external server to be output.

Figure 5:
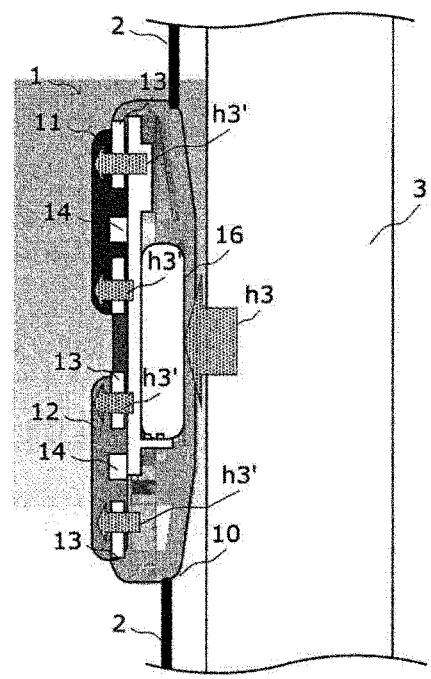
FIG. 5 is a diagram illustrating a specific example in which the solar radiation heat sensor device according to this embodiment is attached to clothes.

Next, referring to FIG. 5, description is given of a model in a case where the solar radiation heat sensor device 1 having the above-mentioned configuration is installed in an environment without solar radiation.

As illustrated in FIG. 5, the solar radiation heat sensor device 1 is attached to the clothes 2, and the user wears the clothes 2. In FIG. 5, a part of the body of the user is illustrated as the human body 3.

The top surface 10a of the casing 10 in the solar radiation heat sensor device 1 is in contact with the outside air, and the bottom surface 10b is in contact with the human body 3. For example, when solar radiation such as sunlight does not reach the solar radiation heat sensor device 1, and the outside temperature is smaller than the body temperature of the human body 3, as indicated by arrows of FIG. 5, a heat h3 generated by the human body 3 is transferred from the bottom surface 10b of the casing 10 to increase the temperature of the casing 10 (arrow h3' of FIG. 5).

In this case, the heat h3 generated by the human body 3 is transferred from the casing 10 to both of the black plate 11 and the silver plate 12. When the structures of the heat insulating materials 13 used for the black plate 11 and the silver plate 12 are equal to each other, the same amount of heat is transferred. When there is no absorption of heat due to radiant heat, the black plate temperature and the silver plate temperature are the same as each other irrespective of the radiation rates of the black plate 11 and the silver plate 12.

Figure 6:
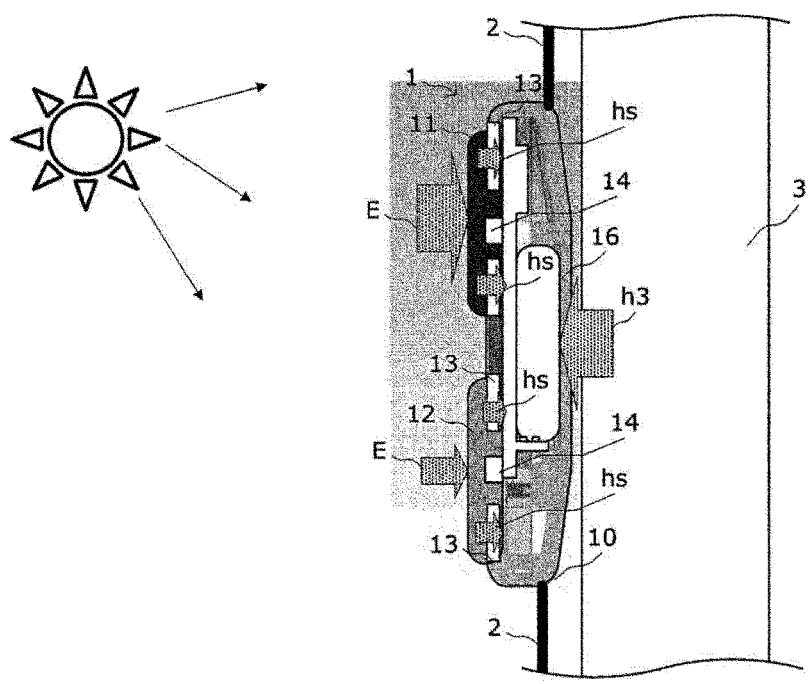
FIG. 6 is a diagram illustrating a specific example in which the solar radiation heat sensor device according to this embodiment is attached to clothes.

On the other hand, referring to FIG. 6, description is given of a model in a case where the solar radiation heat sensor device 1 having the above-mentioned configuration is installed in an environment with solar radiation. As illustrated in FIG. 6, when an electromagnetic wave emitted from the sun reaches the surfaces of the black plate 11 and the silver plate 12, the electromagnetic wave is converted into internal energy to change the temperatures of the black plate 11 and the silver plate 12.

Specifically, when the black plate 11 and the silver plate 12 receive solar radiation, the black plate 11 and the silver plate 12 absorb radiant energy (arrow E), resulting in increase of the temperatures (arrow hs). When the radiant energy from the sun is represented by E, the absorption rate (radiation rate) of the black plate 11 is represented by $\alpha_b$, and the area of the surface is represented by A, energy absorbed by the black plate 11 is represented by $\alpha_b \cdot E \cdot A$. Meanwhile, when the absorption rate of the silver plate 12 is represented by as and the area of the surface is represented by A, energy absorbed by the silver plate 12 is represented by $\alpha_s \cdot E \cdot A$.

The energy absorbed by the black plate 11 and the energy absorbed by the silver plate 12 are proportional to the absorption rates $\alpha_b$ and $\alpha_s$, respectively. As described above, when the absorption rate $\alpha_b$ of the black plate 11 is 0.95 and the absorption rate as of the silver plate 12 is 0.06, the absorption rate $\alpha_b$ of the black plate 11 is about sixteen times as large as the absorption rate $\alpha_s$ of the silver plate 12. As a result, when the surfaces of the black plate 11 and the silver plate 12 receive a larger amount of solar radiation, the temperature difference between the black plate temperature and the silver plate temperature becomes a larger value.

Figure 7:
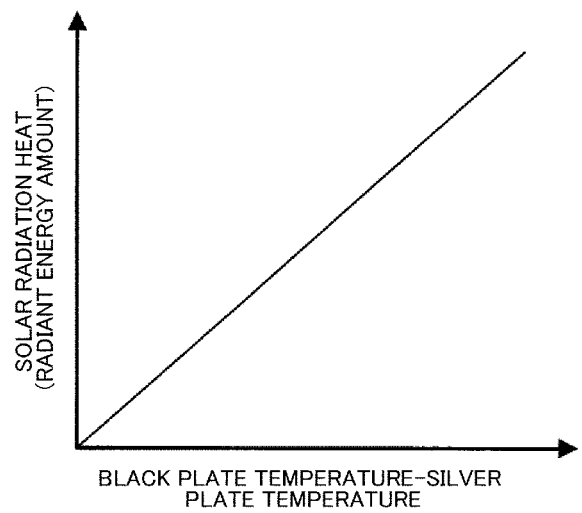
FIG. 7 is a graph describing a relationship between a solar radiation heat amount and a temperature according to this embodiment.

As illustrated in FIG. 7, it is known that a difference between the black plate temperature based on energy absorbed by the black plate 11 and the silver plate temperature based on energy absorbed by the silver plate 12 is approximately proportional to the solar radiation heat amount, namely, a radiant energy amount. The amount of heat transfer from the black plate 11 to the casing 10 and the amount of heat transfer from the silver plate 12 to the casing 10 are different from each other, and thus a completely proportional relationship is not established. However, the accuracy is high enough to estimate the solar radiation heat amount. The relationship between the solar radiation heat amount and the difference between the black plate temperature and the silver plate temperature, which is illustrated in FIG. 7, is stored in the memory 103.

Operation of Solar Radiation Heat Sensor Device

Figure 8:
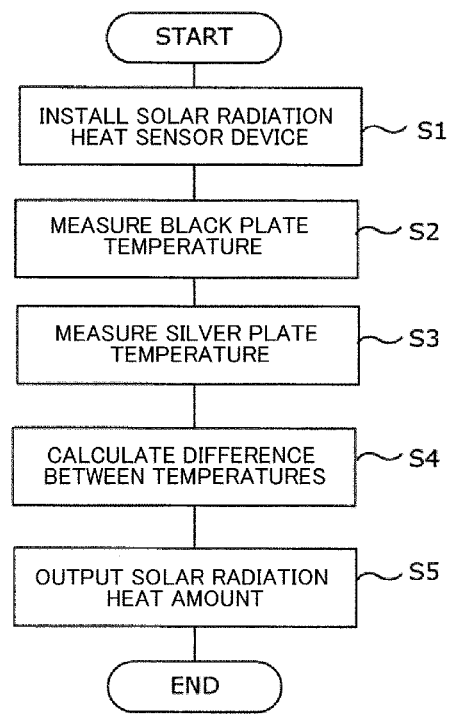
FIG. 8 is a flow chart illustrating an operation of the solar radiation heat sensor device according to this embodiment.

Next, description is given of an operation of the solar radiation heat sensor device 1 according to this embodiment with reference to a flow chart of FIG. 8. First, the solar radiation heat sensor device 1 is attached to the clothes 2, and the user wears the clothes 2 (Step S1).

Next, for example, it is assumed that solar radiation from, for example, the sun reaches the solar radiation heat sensor device 1. The radiant energy E from, for example, the sun is absorbed by the surface of the black plate 11, and the processor 102 outputs a black plate temperature based on a signal indicating a temperature change detected by the thermistor 14 (Step S2). The output black plate temperature is stored in the memory 103.

Next, the radiant energy E from, for example, the sun is transferred to and absorbed by the silver plate 12, and the processor 102 outputs a silver plate temperature based on a signal indicating a temperature change detected by the thermistor 14 (Step S3). The output silver plate temperature is stored in the memory 103.

After that, the processor 102 included in the control board 15 calculates a difference between the black plate temperature and the silver plate temperature (Step S4). The calculated difference between the black plate temperature and the silver plate temperature is stored in the memory 103 of the control board 15.

Next, the processor 102 reads a curve for converting between the solar radiation heat amount and the difference between the black plate temperature and the silver plate temperature, which is illustrated in FIG. 7 and stored in the memory 103 in advance, and outputs a solar radiation heat amount corresponding to the value of the temperature difference calculated in Step S4 (Step S5).

Specific Example

Figure 9:
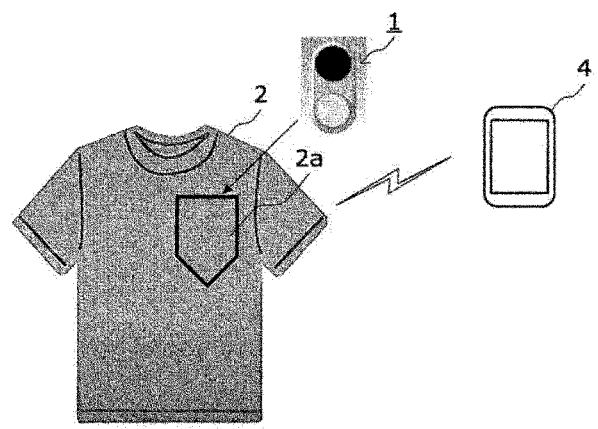
FIG. 9 is a diagram illustrating a specific example in which the solar radiation heat sensor device according to this embodiment is inserted into a pocket of clothes.
Figure 10:
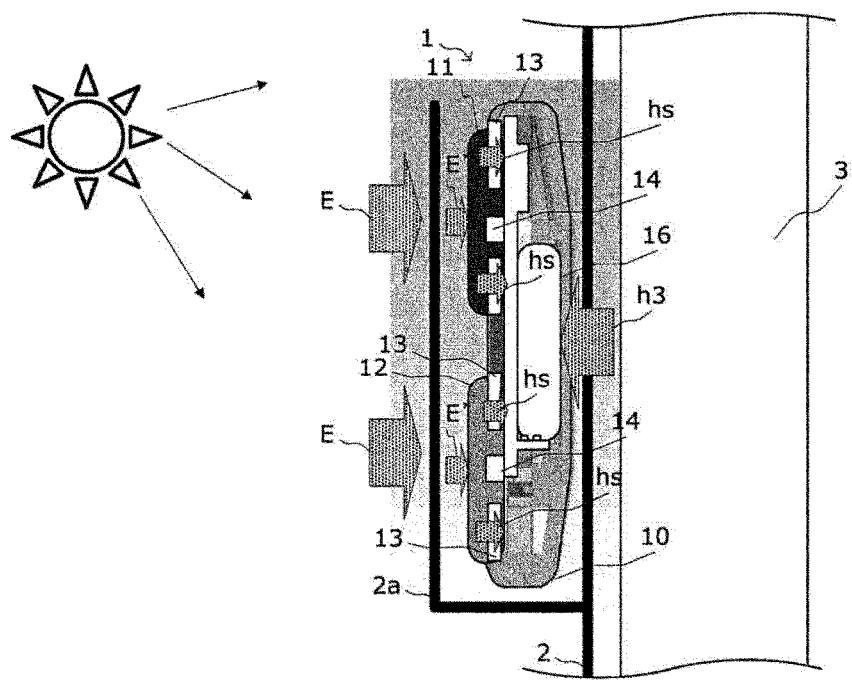
FIG. 10 is a diagram illustrating a specific example in which the solar radiation heat sensor device according to this embodiment is inserted into the pocket of clothes.
Figure 11:
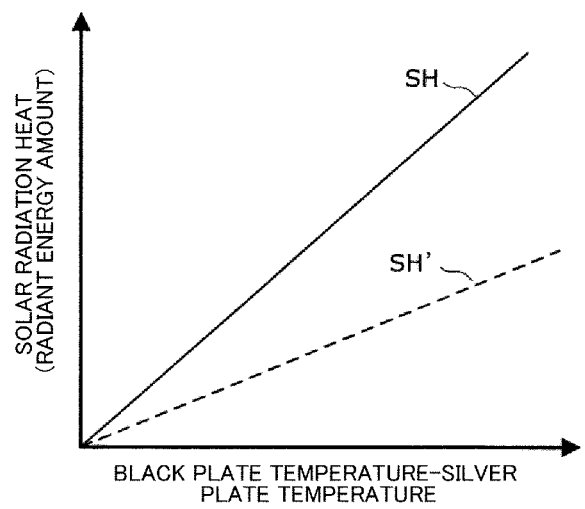
FIG. 11 is a graph describing a relationship between the solar radiation heat amount and the temperature according to a specific example of this embodiment.

Next, referring to FIG. 9 to FIG. 11, description is given of a specific example of inserting the solar radiation heat sensor device 1 having the above-mentioned configuration into a pocket 2a of the clothes 2 worn by the user, and measuring the solar radiation heat amount.

As illustrated in FIG. 9 and FIG. 10, for example, a pocket 2a is provided on a chest part of the clothes 2 worn by the user. The solar radiation heat sensor device 1 is inserted into the pocket 2a such that the black plate 11 and the silver plate 12 face the outside air in the pocket 2a.

In general, the clothes 2 worn by the user are washed after wearing. When the clothes 2 are washed, the solar radiation heat sensor device 1 is required to be removed from the clothes 2. Furthermore, the battery 16 inserted into the inside of the casing 10 of the solar radiation heat sensor device 1 is required to be replaced or charged. In particular, when the communication control circuit 104 is provided on the control board 15, and the solar radiation heat amount is notified to the outside in real time, the power consumption of the battery 16 increases. In that case, the battery 16 is required to be replaced or charged more frequently.

In this manner, in consideration of the necessity for replacing the battery 16, it may be more convenient for the user to insert the solar radiation heat sensor device 1 into the pocket 2a to measure the solar radiation heat amount than to adopt the configuration of attaching the solar radiation heat sensor device 1 to the clothes 2. However, solar radiation that reaches the black plate 11 or the silver plate 12 may be blocked by the cloth of the pocket 2a (arrow E' of FIG. 8), and the sensitivity of temperature measurement may decrease.

In a specific example according to this embodiment, even when solar radiation to be received by the solar radiation heat sensor device 1 is blocked by the cloth of the pocket 2a of the clothes 2, and the amount of radiant energy that reaches the surfaces of the black plate 11 and the silver plate 12 has decreased, the solar radiation heat amount can be calculated by obtaining in advance a transmittance t of heat radiation on the cloth of the pocket 2a and using the transmittance t. More specifically, the energy absorbed by the black plate 11 is represented by $t \cdot \alpha_b \cdot E \cdot A$, and the energy absorbed by the silver plate 12 is represented by $t \cdot \alpha_s \cdot \Sigma \cdot A$.

As illustrated in FIG. 11, regarding the clothes 2 without the pocket 2a, a solar radiation heat amount SH in a case where the cloth does not block solar radiation and the difference between the black plate temperature and the silver plate temperature have a proportional relationship. A solar radiation heat amount SH', which is measured when the cloth of the pocket 2a according to a specific example blocks solar radiation, can be divided by the transmittance t of the pocket 2a obtained in advance, to thereby estimate the solar radiation heat amount SH.

As described above, the solar radiation heat sensor device 1 according to this embodiment uses the difference between the black plate temperature and the silver plate temperature, which is measured based on heat radiation absorbed by the surfaces of the black plate 11 and the silver plate 12. Therefore, it is possible to realize the smaller and lighter solar radiation heat sensor device 1, which can be attached to the clothes 2 of the user without thermally separating the black plate 11 and the silver plate 12 from the casing 10 sufficiently.

In the above, description has been given of the solar radiation heat sensor device and the solar radiation heat measurement method according to an embodiment of the present invention. However, the present invention is not limited to the embodiment described above, and various modifications that could be conceived by a person skilled in the art can be made thereto within the scope of the invention described in the appended claims.

REFERENCE SIGNS LIST

1 Solar radiation heat sensor device
2 Clothes
2a Pocket
3 Human body
4 Terminal
10 Casing
10a Top surface
10b Bottom surface
11 Black plate
12 Silver plate
13 Heat insulating material
14 Thermistor
15 Control board
16 Battery
101 Bus
102 Processor
103 Memory
104 Communication control circuit
105 Input/output device.

The invention claimed is:

1. A solar radiation heat sensor device, comprising:
a first plate having a black surface;
a second plate having a silvery-white surface;
a casing, wherein a first surface of the casing supports the first plate and the second plate in such a manner as to have the black surface and the silvery-white surface facing a same direction and exposed to an outside;
a first heat insulating material between the first plate and the first surface of the casing, wherein the first heat insulating material contacts a back surface of the first plate that is opposite to the black surface;
a temperature sensor in the casing and configured to measure a first temperature of the first plate and a second temperature of the second plate; and
a processor encased by the casing and configured to calculate a solar radiation heat amount based on a difference between the first temperature of the first plate and the second temperature of the second plate as measured by the temperature sensor.

2. The solar radiation heat sensor device according to claim 1, wherein the first plate and the second plate are provided in the casing so as to be separated from each other in a plain view.

3. The solar radiation heat sensor device according to claim 1, wherein the first plate and the second plate have a same shape and size.

4. The solar radiation heat sensor device according to claim 1, wherein the first plate and the second plate each have a disk shape.

5. The solar radiation heat sensor device according to claim 1, further comprising:
a second heat insulating material between the second plate and first surface of the casing, wherein the second heat insulating material contacts a back surface of the second plate that is opposite to the silvery-white surface.

6. The solar radiation heat sensor device according to claim 1, further comprising:
a control circuit including the processor and configured to control an operation of the temperature sensor; and
a battery configured to supply power to the control circuit, wherein the control circuit and the battery are encased by the casing.

7. The solar radiation heat sensor device according to claim 1, further comprising a communication control circuit configured to control communication with the outside.

8. A solar radiation heat measurement method executed by a solar radiation heat sensor device, the solar radiation heat measurement method comprising:
a first step of measuring, by a temperature sensor, a first temperature of a first plate and a second temperature of a second plate, wherein the solar radiation heat sensor device comprises:
the first plate, the first plate having a black surface;
the second plate, the second plate having a silvery-white surface;
a casing, wherein a first surface of the casing supports the first plate and the second plate in such a manner as to have the black surface and the silvery-white surface facing a same direction and exposed to an outside;
a first heat insulating material between the first plate and the first surface of the casing, wherein the first heat insulating material contacts a back surface of the first plate that is opposite to the black surface;
the temperature sensor, the temperature sensor being disposed in the casing; and
a processor, the processor being encased by the casing; and
a second step of calculating, by the processor, a solar radiation heat amount based on a difference between the first temperature of the first plate and the second temperature of the second plate as measured in the first step.

9. The solar radiation heat measurement method according to claim 8 further comprising providing the first plate and the second plate in the casing so as to be separated from each other in a plain view, and wherein a distance between the first plate and the second plate is a maximum distance that the casing can accommodate.

10. The solar radiation heat measurement method according to claim 8, wherein the first plate and the second plate have a same shape and size.

11. The solar radiation heat measurement method according to claim 8, wherein the first plate and the second plate each have a disk shape.

12. The solar radiation heat measurement method according to claim 8, wherein the solar radiation heat sensor device further comprises:
a control circuit including the processor and configured to control an operation of the temperature sensor; and
a battery configured to supply power to the control circuit, wherein the control circuit and the battery are encased by the casing.

13. The solar radiation heat measurement method according to claim 8, wherein the solar radiation heat sensor device further comprises a communication control circuit configured to control communication with the outside.

14. The solar radiation heat measurement method according to claim 8, wherein the solar radiation heat sensor device further comprises:
a second heat insulating material between the second plate and the first surface of the casing, wherein the second heat insulating material contacts a back surface of the second plate that is opposite to the silvery-white surface.

15. The solar radiation heat sensor device according to claim 1, wherein the first heat insulating material has a periphery that matches the first plate in a top-down view.

16. The solar radiation heat sensor device according to claim 1, wherein the first heat insulating material comprises a hole in a center of the first heat insulating material, and wherein the temperature sensor is disposed in the hole.

17. The solar radiation heat sensor device according to claim 16, wherein the first plate extends into the hole of the first heat insulating material and is disposed along sidewalls of the temperature sensor.

18. The solar radiation heat sensor device according to claim 1, further comprising a stud of a snap button on a second surface of the casing, the second surface of the casing being opposite to the first surface of the casing, wherein the stud of the snap button is configured to be attached to a buckle of the snap button, the buckle of the snap button being disposed on an article of clothing.

* * * * *